April 11, 1972 G. V. SCHICHTEL Plant Pat. 3,109
MAPLE TREE
Filed Dec. 11, 1969
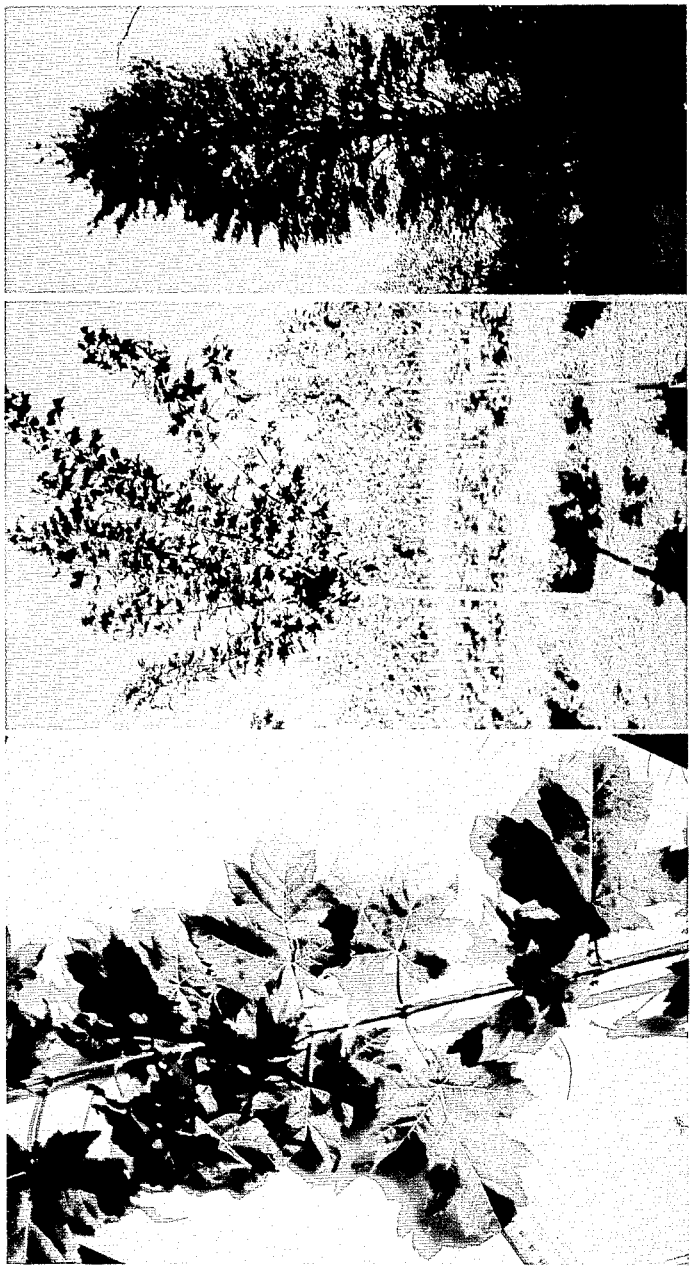
Inventor.
George V. Schichtel
By: Robb & Robb
Attorneys.

United States Patent Office

Plant Pat. 3,109
Patented Apr. 11, 1972

3,109

MAPLE TREE

George V. Schichtel, Orchard Park, N.Y., assignor to J. Frank Schmidt & Son Co., Troutdale, Oreg.

Filed Dec. 11, 1969, Ser. No. 884,388
Int. Cl. A01h *5/12*
U.S. Cl. Plt.—51 1 Claim

The present invention relates to a new and distinct variety of maple tree of the species botanically known as *Acer rubrum,* which was discovered by me as a natural seedling of unknown parentage occurring on cultivated property located at Ashtabula, Ohio.

At the time of my discovery, my attention was attracted to this seedling by its exceptional vigor and distinctively upright habit of growth, as was apparent from the mature tree which was growing in an open field apart from other nursery trees being grown on this property at Ashtabula. I immediately requested and was given permission to take bud wood therefrom and arranged to have it propagated, as performed on my behalf by budding at Troutdale, Oreg.

Continued and prolonged tests and observations of the progeny derived from these buddings have confirmed that the exceptional vigor and upright form of the tree come true and are established and transmitted through succeeding propagations.

These tests and prolonged observations have further established that my new seedling is the most vigorous of all other upright maples of which I am aware, with its growth extending late in the season, and the trees being distinctively distinguished from other maples of this type by their very smooth and shiny bark. Otherwise, my new seedling generally is typical of the species. The distinguishing features afore-mentioned represent commercially valuable improvements in the species, and make my new seedling more advantageously suited for street, highway and lawn plantings where rapid growth and an upright tree form are most desirable.

The accompanying drawing shows a mature tree specimen depicting the upright form of my new seedling, as well as a young tree of about 2 years of age, together with a typical branch segment bearing typical foliage depicted on a larger scale and illustrating the color thereof.

While the exceptionally vigorous habit, upright form and very smooth and shiny bark of my new maple variety are the principal distinctive features thereof, the following brief detailed description is given for convenience, with color terminology in accordance with Nickerson's Color Fan, published by Munsell Color Company, Inc., of Baltimore, Md., except where general color terms of ordinary dictionary significance are obvious:

Parentage: Seedling of unknown parentage.
Propagation: Holds its distinguishing characteristics through succeeding propagations by budding.
Locality where grown and observed: Troutdale, Oreg.
Tree: Medium size; upright; tall but terminating in a rounded head at the top; hardy.
*Trunk.*—Stocky; medium smooth; very smooth and shiny bark. Color.—Light grey, turning to blackish grey where furrows begin.
*Branches.*—Slender; smooth. Color.—New growth—Lustrous dark red. Older branches—Near Moderate Yellowish Brown, Hue 10 YR 4/4, and then turning to grey as branches age. Lenticels—Abundant; prominent; minute.

Foliage:
*Leaves.*—Texture—Exceptionally heavy. Quantity—Very abundant. Size—Length—From about 4 inches to 5 inches. Width—Approximately 4 inches. Shape—Palmately 3-lobed but some distinctly 5-lobed. Color—Upper side—Near Moderate Yellow Green, Hue 7.5 GY 5/7. Underside—Lighter silvery glaucous near Very Pale Green, Hue 7.5 G 9/2. Fall Color—Red. Margin—Serrate. Petiole—Medium length. Glands—Normal for the species.
Flower buds:
*Hardiness.*—Good (zone 5).
*Size.*—About ⅛ inch in diameter.
*Shape.*—Round.
*Color.*—Dark red.
Flowers:
*Dates of first and full bloom.*—About April 1 and April 15, respectively, at Troutdale, Oreg.
*Quantity.*—Abundant.
*Size.*—Small.
*Color.*—Red.

*General observations*

The shape of the tree of this new maple variety is distinctly columnar, but it has a rounded head or crown at the top contrary to relatively sharp-pointed tops of such varieties as "Scanlon" maple (which is normally classified as a conical maple, "Armstrong II" maple (which is a spire-like type), or "Bowhall" maple (which is noted for its conical or pyramidal shape). Field tests and comparisons in the nursery fields of my assignee have shown that the new variety is definitely a much stronger grower than any of those varieties, as well as the variety known as *A. rubrum* columnare. This exceptionally stronger growth is probably attributable to the fact that the growth of the new variety continues and extends well into late summer (late August in Oregon), while the other varieties show a marked decline in the rate of growth much earlier (columnare as early as May; "Bowhall"-"Scanlon" as early as July; and "Armstrong" in early August) all as grown under the same conditions in Oregon. Accordingly, of all of the upright red maples commonly grown commercially, the new variety can be truly considered to be the most vigorous. Also, the significantly heavier texture of its foliage enables it to be grown more widely in geographical areas which have a greater temperature range. This combination of the foregoing characteristics greatly enhances the commercial value of the new variety, and characterizes it as a new and distinct variety.

I claim:

1. A new and distinct variety of maple tree of the type bontanically known as *Acer rubrum,* substantially as herein shown and described, characterized particularly as to novelty by an exceptionally vigorous habit of growth which extends late in the growing season, an upright form terminating in a rounded head at the top of the tree, and having very smooth and shiny bark, and attractive light green foliage of heavy texture and distinctive shape, and which turns red in the fall, while otherwise generally having characteristics usually typical of the species *Acer rubrum.*

References Cited

Scanlon Tailored Trees, Spring-Fall 1967, pp. 26 and 30 relied on.

Coles Spring Trade List 1962, Frontispiece and pp. 4–5 relied on.

ROBERT E. BAGWILL, Primary Examiner